(12) United States Patent
Wollenweber et al.

(10) Patent No.: US 8,879,814 B2
(45) Date of Patent: Nov. 4, 2014

(54) METHOD AND APPARATUS FOR REDUCING MOTION RELATED IMAGING ARTIFACTS USING CONSISTENCY VALUES

(75) Inventors: Scott David Wollenweber, Waukesha, WI (US); Adam Alessio, Seattle, WA (US); Paul Kinahan, Seattle, WA (US)

(73) Assignees: General Electric Company, Schenectady, NY (US); University of Washington, Seattle, WA (US)

( * ) Notice: Subject to any disclaimer, the term of this patent is extended or adjusted under 35 U.S.C. 154(b) by 276 days.

(21) Appl. No.: 13/477,218

(22) Filed: May 22, 2012

(65) Prior Publication Data
US 2013/0315459 A1    Nov. 28, 2013

(51) Int. Cl.
*G06K 9/00*    (2006.01)

(52) U.S. Cl.
USPC .......................................................... 382/131

(58) Field of Classification Search
None
See application file for complete search history.

(56) References Cited

U.S. PATENT DOCUMENTS

| | | | |
|---|---|---|---|
| 7,043,063 B1 * | 5/2006 | Noble et al. .................. | 382/128 |
| 7,254,259 B2 | 8/2007 | Hsieh et al. | |
| 7,348,564 B2 | 3/2008 | Wollenweber et al. | |
| 7,652,259 B2 * | 1/2010 | Kimchy et al. .......... | 250/370.08 |
| 7,729,467 B2 | 6/2010 | Kohlmyer et al. | |
| 8,098,916 B2 * | 1/2012 | Thielemans et al. .......... | 382/131 |
| 2006/0237652 A1 * | 10/2006 | Kimchy et al. .......... | 250/363.02 |
| 2008/0265166 A1 * | 10/2008 | Shekhar et al. .......... | 250/363.03 |
| 2009/0110256 A1 * | 4/2009 | Thielemans et al. .......... | 382/131 |
| 2012/0051664 A1 | 3/2012 | Gopalakrishnan et al. | |
| 2012/0078089 A1 * | 3/2012 | Wollenweber et al. ........ | 600/427 |
| 2013/0315459 A1 * | 11/2013 | Wollenweber et al. ........ | 382/131 |

OTHER PUBLICATIONS

Attenuation-emission alignment in cardiac PET/CT based on consistency conditions, Adam M. Allessio, Feb. 19, 2010, American Association of Physicists in Medicine.

* cited by examiner

*Primary Examiner* — Tahmina Ansari
(74) *Attorney, Agent, or Firm* — Dean D. Small; The Small Patent Law Group

(57) ABSTRACT

A method for reducing, in an image, motion related imaging artifacts. The method includes obtaining a single image of a subject using a computed tomography (CT) imaging system, obtaining a plurality of images of the subject using a positron emission tomography (PET) imaging system, generating a plurality of consistency values, and utilizing the plurality of consistency values to register the CT image and the plurality of PET images.

20 Claims, 6 Drawing Sheets

| US 8,879,814 B2

METHOD AND APPARATUS FOR REDUCING MOTION RELATED IMAGING ARTIFACTS USING CONSISTENCY VALUES

BACKGROUND OF THE INVENTION

The subject matter disclosed herein relates generally to imaging systems, and more particularly to an apparatus and method for motion-correcting medical images.

Multi-modality imaging systems scan using different modalities, for example, computed tomography (CT) and positron emission tomography (PET) imaging. During operation, the image quality may be affected by the motion of the object being imaged. More specifically, image artifacts are produced by movement of the object during image acquisition. Respiratory motion is a common source of involuntary motion in mammals (e.g., people and animals) encountered in medical imaging systems. The respiratory motion may lead to errors during image review, such as when a physician is determining the size of a lesion, determining the location of the lesion, or quantifying the lesion.

Moreover, in multi-modality systems, for example, an integrated PET/CT system, the PET and CT images should be registered with one another. However, since the CT images are typically acquired during a short time period, the attenuation map generated by the CT images represents the attenuation characteristics of the patient during a portion of the breathing cycle where there is minimal breathing motion. In contrast, the PET images are typically acquired over a relatively long time period where a patient is allowed to breathe freely due to the long acquisition time. The mismatch in attenuation properties due to respiration between the two data acquisition modes may result in image artifacts in the attenuation corrected PET images.

One known method for reducing the imaging artifacts is to use a plurality of respiratory gated CT images to generate attenuation correction maps that better match the respiratory characteristics of a respiratory gated PET acquisition. A further method may include requesting the patient to hold their breath during the scan. However, because PET data may be acquired over several minutes, the patient typically has to breathe several times during the PET acquisition, potentially resulting in image artifacts.

BRIEF DESCRIPTION OF THE INVENTION

In one embodiment, a method for reducing, in an image, motion related imaging artifacts is provided. The method includes obtaining a single, motion-reduced image of a subject using a computed tomography (CT) imaging system, obtaining a plurality of images of the subject using a positron emission tomography (PET) imaging system, generating a PET motion correction, generating a plurality of attenuation consistency values, utilize the plurality of consistency values to match the CT image to a PET image, transform the CT image using the PET motion correction to match the other PET images and re-calculate the plurality of PET images.

In another embodiment, a dual-modality imaging system is provided. The dual-modality imaging system includes a computed tomography (CT) imaging system, a positron emission tomography (PET) imaging system, and a processor coupled to the CT and PET imaging systems. The processor is configured to obtain a single image of a subject using the CT imaging system, obtain a plurality of images of the subject using the PET imaging system, generate a PET motion correction, generate a plurality of attenuation consistency values, utilize the plurality of consistency values to register the CT image and the plurality of PET images and then re-calculate the plurality of PET images.

In a further embodiment, a non-transitory computer readable medium is provided. The non-transitory computer readable medium is encoded with a program programmed to instruct a computer to obtain a single image of a subject using a computed tomography (CT) imaging system, obtain a plurality of images of the subject using a positron emission tomography (PET) imaging system, generate a plurality of consistency values, and utilize the plurality of consistency values to register the CT image and the plurality of PET images.

DETAILED DESCRIPTION OF THE INVENTION

Figure 1:
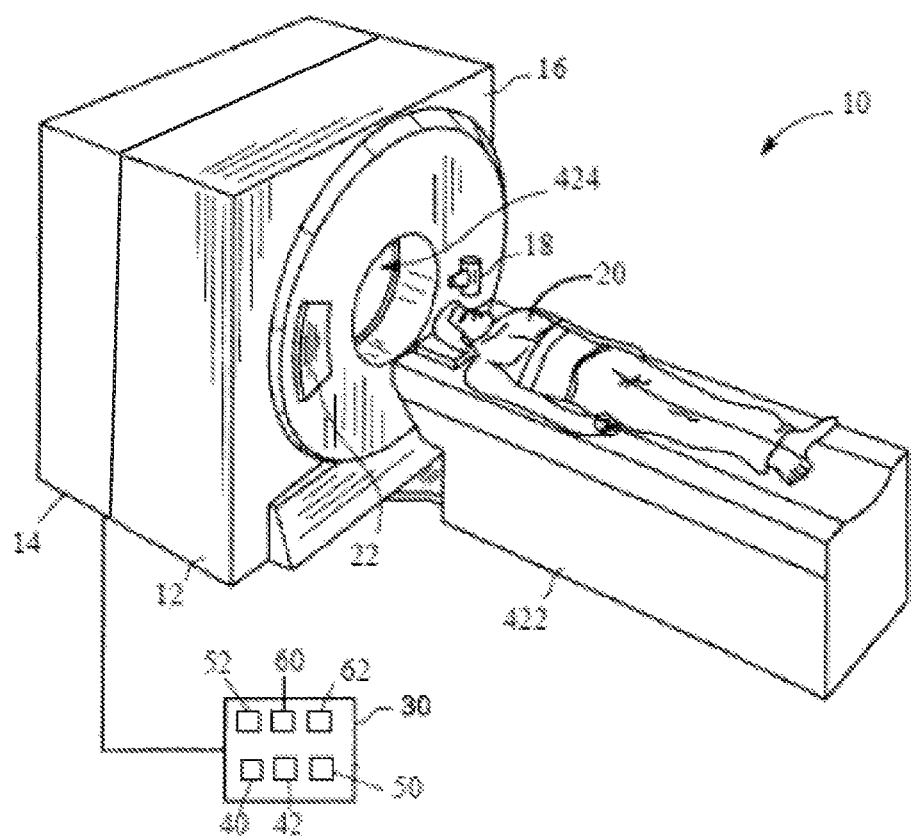
FIG. 1 is a pictorial illustration of an exemplary imaging system formed in accordance with various embodiments.

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

FIG. 1 is a perspective view of an exemplary imaging system 10 that may be configured to implement the various embodiments described herein. Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used.

The multi-modality imaging system 10 includes a CT imaging system 12 and a PET imaging system 14. The imaging system 10 allows for multiple scans in different modalities to facilitate an increased diagnostic capability over single modality systems. Optionally, modalities other than CT and PET are employed with the imaging system 10. The CT imaging system 12 includes a gantry 16 that has an x-ray source 18 that projects a beam of x-rays through a subject 20. After being attenuating by the subject 20, the x-rays impinge on a detector 22 located on the opposite side of the gantry 16. The imaging system 10 also includes a computer 30 that receives an attenuation projection dataset 40 using the CT imaging system 12 and an emission projection data set 42 from the PET imaging system 14. The imaging system 10 may also include a memory 52. The memory 52 may be located internally within the computer 30 as illustrated in FIG. 1. Optionally, the memory 52 may be a storage device that is located remotely from the imaging system 10. In operation, the computer 30 processes the attenuation projection data 40 and the emission projection data 42 to reconstruct images of the subject 20.

The imaging system 10 also includes an image reconstruction module 50 that is configured to implement various methods described herein. The module 50 may be implemented as a piece of hardware that is installed in the computer 30. Optionally, the module 50 may be implemented as a set of instructions that are installed on the computer 30. The set of instructions may be stand alone programs, may be incorporated as subroutines in an operating system installed on the computer 30, may be functions in an installed software package on the computer 30, and the like. It should be understood that the various embodiments are not limited to the arrangements and instrumentality shown in the drawings.

Figure 2:
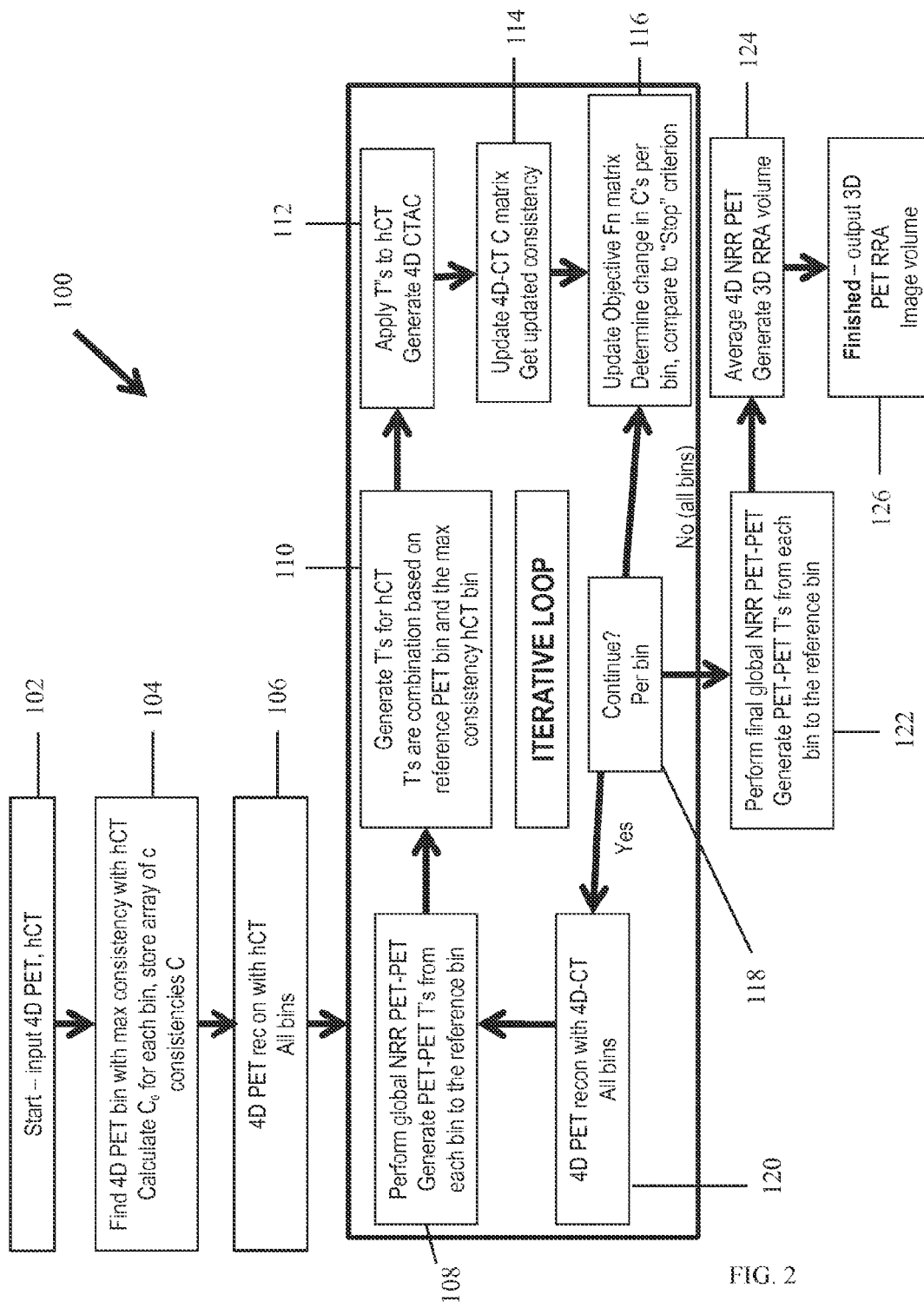
FIG. 2 is a flowchart illustrating a method for reducing motion related imaging artifacts in accordance with various embodiments.

FIG. 2 is a block diagram of an exemplary method 100 performed by the imaging system 10 shown in FIG. 1. In the exemplary embodiment, the method 100 may be implemented using the image reconstruction module 50. More specifically, the method 100 may be provided as a machine-readable medium or media having instructions recorded thereon for directing the processor 30 and/or the image reconstruction module 50 to perform an embodiment of the method described herein. The medium or media may be any type of CD-ROM, DVD, floppy disk, hard disk, optical disk, flash RAM drive, or other type of computer-readable medium or a combination thereof.

At 102, the attenuation projection dataset 40 and emission projection dataset 42 of the subject 20 (each shown in FIG. 1) are input to the image reconstruction module 50. In the exemplary embodiment, the attenuation projection dataset 40 is obtained using the CT imaging system 12 (shown in FIG. 1). The attenuation projection dataset 40 may be obtained by performing a scan of the subject 20 to produce the attenuation projection dataset 40. Optionally, the attenuation projection dataset 40 may be obtained from data collected during a previous scan of the subject 20, wherein the attenuation projection dataset 40 has been stored in a memory, such as the memory device 52 (shown in FIG. 1). The attenuation projection dataset 40 may be stored in any format, such as a list mode dataset, for example. The attenuation projection dataset 40 may be obtained during real-time scanning of the subject 20. For example, the methods described herein may be performed on projection data as the attenuation projection dataset 40 is received from the CT imaging system 12 during a real-time examination of the subject 20. In various embodiments, the attenuation projection dataset 40 is a single snapshot or a single image 60 (as shown in FIG. 1) of the subject 20 acquired during a short time interval during the CT scan. The single image 60 may be acquired, for example, during a CT helical scan. Thus, the single CT image 60 is labeled as (hCT) in FIG. 2 to denote that in the illustrated embodiment, the single image 60 is acquired during a helical scan of the subject 20. Acquiring just enough attenuation projection data 40 to generate the single CT image 60 facilitates reducing the time required to scan the subject 20 and therefore also reduces the dosage to the subject 20 during the scan.

Additionally, at 102, the emission dataset 42 of the subject 20 (each shown in FIG. 1) is obtained. In the exemplary embodiment, the emission dataset 42 is obtained using the PET imaging system 14 (shown in FIG. 1). The emission dataset 42 may be obtained by performing an emission scan of the subject 20 to produce the emission dataset 42. Optionally, the emission dataset 42 may be obtained from data collected during a previous scan of the subject 20, wherein the emission dataset 42 has been stored in a memory, such as the memory device 52 (shown in FIG. 1). The emission dataset 42 may be stored in any format, such as a list mode dataset, for example. The emission dataset 42 may be obtained during real-time scanning of the subject 20. For example, the methods described herein may be performed on emission data as the emission data 42 is received from the PET imaging system 14 during a real-time examination of the subject 20. In various embodiments, the emission dataset 42 generally includes a plurality of PET images 62 (as shown in FIG. 1) that are, or have been, acquired over a predetermined length of time and segmented into bins ('4D') representing the various positional radiotracer distribution information available during the respiratory cycle. Thus, in the illustrated embodiment, at 102 a single CT image 60 is acquired at a single point in time and a plurality of 40 PET images 62 are acquired over a plurality of different points in time.

Figure 3:
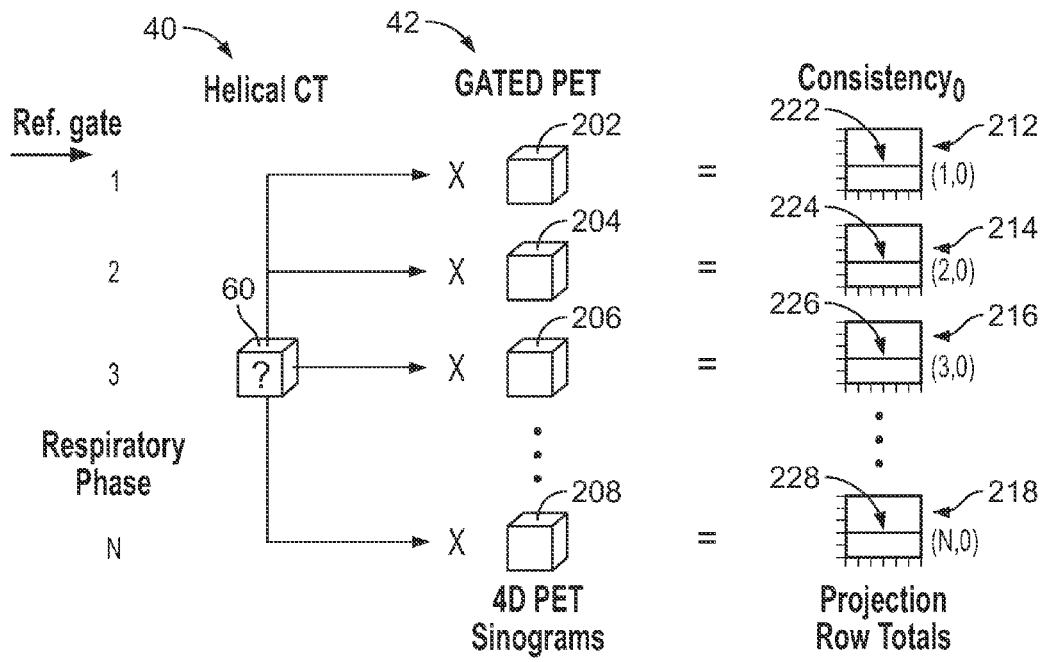
FIG. 3 is a simplified block diagram illustrating a portion of the method shown in FIG. 2.

At 104, a PET bin having a maximum consistency with the CT image 60 is identified. Maximum consistency can be computed, for example, using:

$$\Phi_{m,k} = \int_{\phi}^{2\pi} \int_{-\infty}^{+\infty} s^m e^{ik\phi} e^{A(s,\phi)} E(s,\phi) ds d\phi \qquad \text{Eq. 1}$$

where $E(s,\phi)$ are the measured emission data, $A(s,\phi)$ are the measured projections of the attenuation image, in $m \geq 0$ is the moment being computed and k is the Fourier component. The radial distance from the center of rotation s and the azimuthal angle of rotation $\phi$ index the Radon transform space. FIG. 3 is a flowchart illustrating the method of identifying the PET bin having the maximum consistency with the CT image 60. In various embodiments, the emission dataset 42 is a plurality of sinograms or sinogram data (not shown). The sinogram dimension is based on the number of detectors installed in the PET imaging system 14, and the number of bins containing sinograms varies based upon the user-prescribed respiratory binning protocol. The sinograms may be generated by operating the PET imaging system 14 in a sinogram mode. Sinogram mode generally refers to an acquisition mode in which annihilation events, optionally having an identical Time-of-Flight (TOF), are stored in sinograms in an (radius from axis, angle) format. The array of responses is known as a sinogram. It should be realized that other methods and/or devices may be used for data storage and that the sinograms described herein represent one such exemplary method of storing data.

Accordingly, at 104, the emission dataset 42, e.g. the sinograms, is temporally sorted into a plurality of bins (n bins 200). The emission dataset 42 may be sorted into the bins 200 using respiratory motion, cardiac motion, patient motion, etc. For example, FIG. 3 illustrates n bins 200 numbered 202 . . . 208, i.e. n=4 bins that may be generated in accordance with various embodiments described herein. However, it should be realized that the quantity of bins 200 illustrated in FIG. 3 is exemplary, and that during operation, fewer than four bins or more than four bins may be utilized. As such, each bin 202, 204, 206, and 208 includes approximately ¼ of the total information in the emission dataset 42. For example, assume that the total length of the scan performed by the PET imaging system 14 to acquire the emission dataset 42 is three minutes. Moreover, assume that the emission dataset 42 is sorted into four bins 200. Accordingly, each bin 200 includes approximately 45 seconds of information.

In the exemplary embodiment, after the emission dataset 42 is sorted into the bins 200, a consistency condition is calculated using Eq. 1 for each respective bin 200. More specifically, at 104, the image reconstruction module 50 and/or the processor 30 is configured to determine how well the CT image 60 matches with the sinogram data stored in each respective bin 200 by generating a consistency condition for each respective bin 200.

Figure 5:
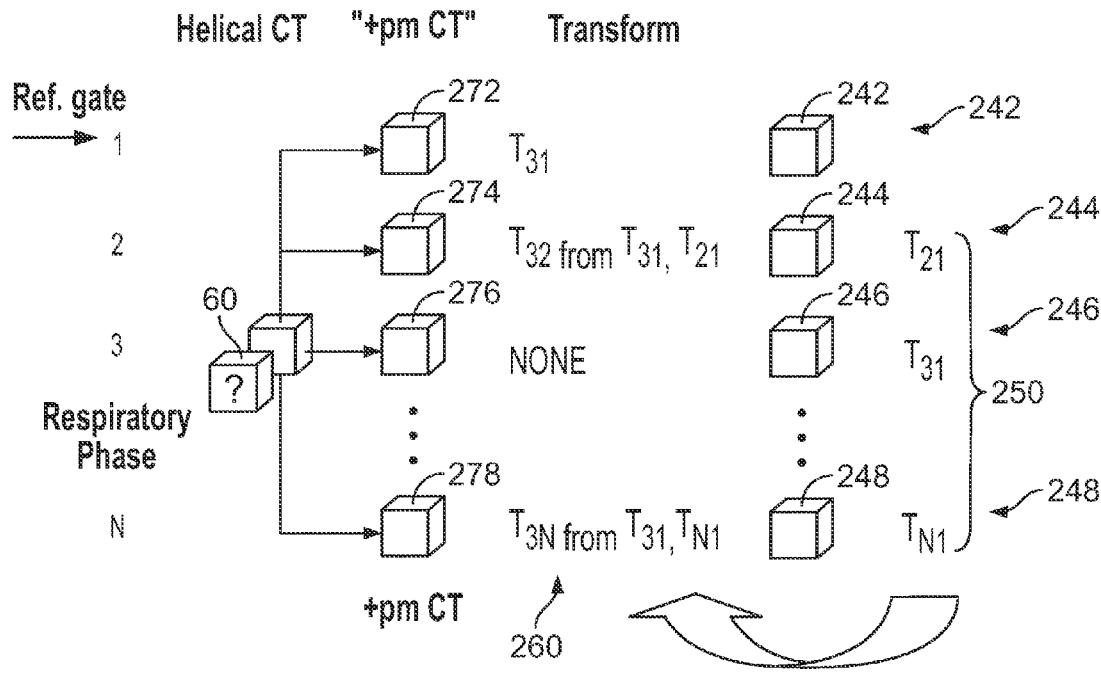
FIG. 5 is a simplified block diagram illustrating another portion of the method shown in FIG. 2.

A consistency value, as used herein, is a value that represents a sum of the projection data from one view of the projection dataset 40 and is independent of the view-angle. More specifically, a consistency value is a sum, or row-sum of all the emission data acquired in one view and is view angle independent. The consistency condition may be calculated using, for example, a Helgason-Ludwig consistency condition (HLCC) algorithm (Eq. 1). As shown in FIG. 3, the graph 212 illustrates the consistency conditions for the bin 202, wherein the x-axis represents the view angle, and the y-axis represent the row-sum of the data. Similarly, the graph 214 illustrates the consistency conditions for the bin 204, the graph 216 illustrates the consistency conditions for the bin 206, and the graph 218 illustrates the consistency conditions for the bin 208. In various embodiments, the consistency conditions for each bin 200 may be calculated but not displayed. These consistency conditions based on the hCT help define the combinations of PET-based transformation necessary to transform the hCT to best match the bins of PET data (shown in a later processing step, FIG. 5).

In various other embodiments, the consistency values for each bin 200 may be calculated and displayed using for example, the graphs 212, 214, 216, and 218. In operation, if the attenuation data 40 is consistent with the emission data 42, a row sum of the attenuation corrected emission data is calculated, and the resulting consistency values, if plotted in a graphical format, should be relatively linear and flat. For example, as shown in FIG. 3, the consistency conditions for the bin 202 are plotted as a line 222 in the graph 212. Moreover, the consistency values for the bin 204 are plotted as a line 224 in the graph 214, the consistency values for the bin 206 are plotted as a line 226 in the graph 216, and the consistency values for the bin 208 are plotted as a line 228 in the graph 218. Accordingly, in various embodiments, the image reconstruction module 50 and/or the processor 30 is configured to automatically determine the consistency conditions for the sinogram data stored in each bin 200. Moreover, the image reconstruction module 50 and/or the processor 30 are further configured to automatically identify which set of consistency conditions are maximized. Maximized as used herein means the consistency conditions are linear or the line shown in one of the graphs 212-218 is the flattest which denotes the best consistency match between the emission data in a single bin 200 and the transmission dataset 40. Accordingly, at 104 a single bin 200 having the maximum consistency values is identified. This identification may include use of an objective function which calculates the total deviation from flatness for each consistency calculation 212, 214, 216, 218. To further explain the methods described herein, in the illustrated embodiment, the bin 206 is selected as having emission data that is the best consistency match between with the transmission dataset 40 and may be referred to herein as the reference bin.

Figure 4:
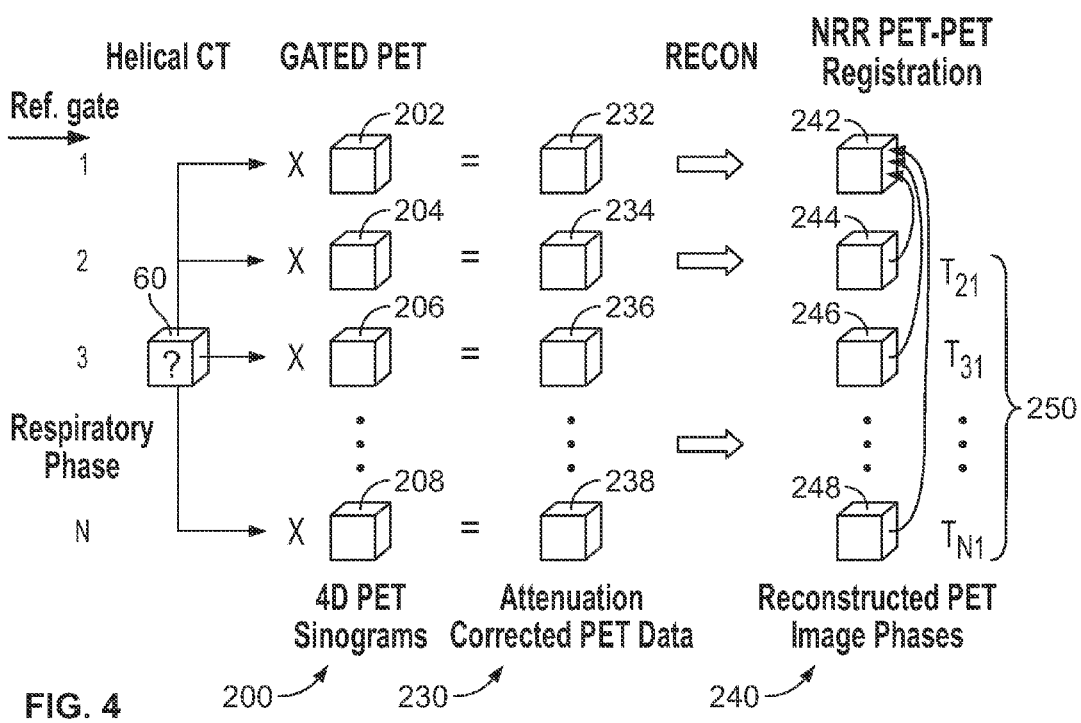
FIG. 4 is a simplified block diagram illustrating another portion of the method shown in FIG. 2.

Referring again to FIG. 2, at 106 the emission projection data in each of the bins is attenuation corrected to generate a plurality of attenuation-corrected PET image datasets. FIG. 4 illustrates a plurality of attenuation-corrected projection datasets 230 that may be generated. For example, at 106 an attenuation-corrected dataset 232 may be generated using information in the bin 202. Similarly, an attenuation-corrected dataset 234 may be generated using information in the bin 204, an attenuation-corrected dataset 236 may be generated using information in the bin 206, and an attenuation-corrected dataset 238 may be generated using information in the bin 208. Accordingly, an attenuation corrected dataset 230 is generated for each respective bin 200.

Additionally, at 106 the attenuation-corrected datasets 230 are utilized to reconstruct a plurality of PET images 240. For example, the attenuation-corrected dataset 232 may be utilized to reconstruct a PET image 242. Similarly, the attenuation-corrected dataset 234 may be utilized to reconstruct a PET image 244, the attenuation-corrected dataset 236 may be utilized to reconstruct a PET image 246, and the attenuation-corrected dataset 238 may be utilized to reconstruct a PET image 248. Accordingly, in various embodiments, a PET image 240 is reconstructed from each attenuation corrected dataset 230.

Referring again to FIG. 2, at 108 a global non-rigid registration of the PET images 242-248 is performed to motion correct the PET images. This process generates transformations on a bin-to-bin basis of the non-rigid registration between all bins not identified as the reference bin and the reference bin. This registration may be performed in image space. The non-rigid registration may be performed manually by the operator or automatically by the processor 30. It should be realized, that registration may not be required in certain areas where there is little or no motion.

In the exemplary embodiment, performing a non-rigid registration includes transforming the information within the bins, i.e. the PET images 242-248, in three-dimensional (3D) space to align the information within the bins 242-248 with respect to a reference bin. To perform the non-rigid registration, at least one of the bins 242-242 is selected as a reference bin and the remaining bins are then registered one-by-one to the reference bin. In various embodiments, the PET image generated from the bin having the best consistency with the CT image 60 is selected as the reference gate. Accordingly, in the illustrated embodiment shown in FIG. 4, the attenuation-corrected dataset 232, which is derived from the information in the bin 202 and used to reconstruct the PET image 242, is used as the reference bin. Therefore, in the illustrated embodiment, the PET images 244, 246 and 248 are registered with respect to the PET image 242.

For example, the PET image 246 may be slighted tilted with respect to the PET image 242. Accordingly, the PET image 246 is tilted to align the images with the PET image 242. The remaining images 244 and 248 are also realigned to substantially match the PET image 242. In operation, the non-rigid registration procedure may be utilized to perform the motion correction on the information within the PET images 242-248. In operation, the non-rigid registration or elastic registration may also include non-rigid transformations. These non-rigid transformations allow local warping of image features and provide registrations that account for local deformations. Non-rigid transformation approaches include, for example, polynomial warping, interpolation of smooth basis functions (thin-plate splines and wavelets), and physical continuum models (viscous fluid models and large deformation diffeomorphisms). Accordingly, in various embodiments, a plurality of transformation matrices is generated to perform the non-rigid registration of the plurality of PET images 242-248 to generate n image volumes.

Accordingly, at 108, a plurality of deformation vectors 250, or transformation matrices are generated using the gated 4D image data, images 242-248. As discussed above, each 3D PET image 242-248 includes a plurality of voxels that are points in three-dimensional space that can be referenced using three-dimensional coordinates, usually x, y and z. A deformation vector represents a motion and/or deformation of the object or voxel(s) of interest, such as the motion of the patient 20, at a certain point of time, with respect to the reference location. Specifically, for each image voxel and for each image 242-248, the vector magnitude [v] (or set of magnitudes) and components [x,y,z], referred to herein as the deformation components, are stored in the memory. In the exemplary embodiment, at 108, a reference image from the 4D image data set is selected. In the illustrated embodiment, the PET image 242 is selected as the reference image. The remaining bins or images 244-248 are then mapped to the reference bin or image 242 to generate the motion deformation vectors In the illustrated example shown in FIG. 4, the PET image 242 is selected as the reference image or gate. Accordingly, in one such example, based on the registration transformation, a set of transformation vectors 250 may be obtained that describe the motion of each respective gate relative to the reference gate. For example, the vectors $T_{21}$ describe the motion differences between the reference PET image 242 and the PET image 244. Moreover, the vectors $T_{31}$ describe the motion differences between the reference PET image 242 and the PET image 246, and the vectors $T_{N1}$ describe the motion differences between the reference PET image 242 and the PET image 248. Accordingly, at step 108, a plurality of motion vectors are acquired and utilized to register the PET images 244-248 to a selected reference image 242.

Referring again to FIG. 2, at 110, a plurality of transformation vectors (T's) are generated using the reference PET bin and the hCT data. In the illustrated example shown in FIG. 5, a set of transformation vectors 260 may be obtained that describe the motion of each respective gate relative to the reference gate based upon the PET-PET transformation data and knowledge of which PET bin the hCT is most consistent with (from FIG. 3). For example, the vectors $T_{31}$ describe the motion differences between the reference PET image 206 and the PET image 202 and may be utilized to generate respiratory phase-matched CT image 272. Moreover, the vectors $T_{32}$ derived from the combination of $T_{31}$ and $T_{21}$, describe the motion differences between the reference PET image 206 and the PET image 204 and may be utilized to generate a respiratory phase-matched CT image 274, and the vectors $T_3N$, derived from $T_{31}$ and $T_{N1}$, describe the motion differences between the reference PET image 206 and the PET image 208. Accordingly, at step 110, a plurality of motion vectors 252 are acquired and at step 112, the plurality of vectors 252 are utilized to transform the CT image 60 to be better attenuation-matched to the PET data 202-208.

More specifically, the plurality of transformation vectors generated at 108 are utilized to map or register the PET images 242-248 to generate a plurality of phase-matched CT images. More specifically, because it is calculated via consistency which PET bin the attenuation map (CT image 60) was closest to, the transformation matrices or vectors acquired at 108 may be utilized to generate the phase-matched images.

Figure 6:
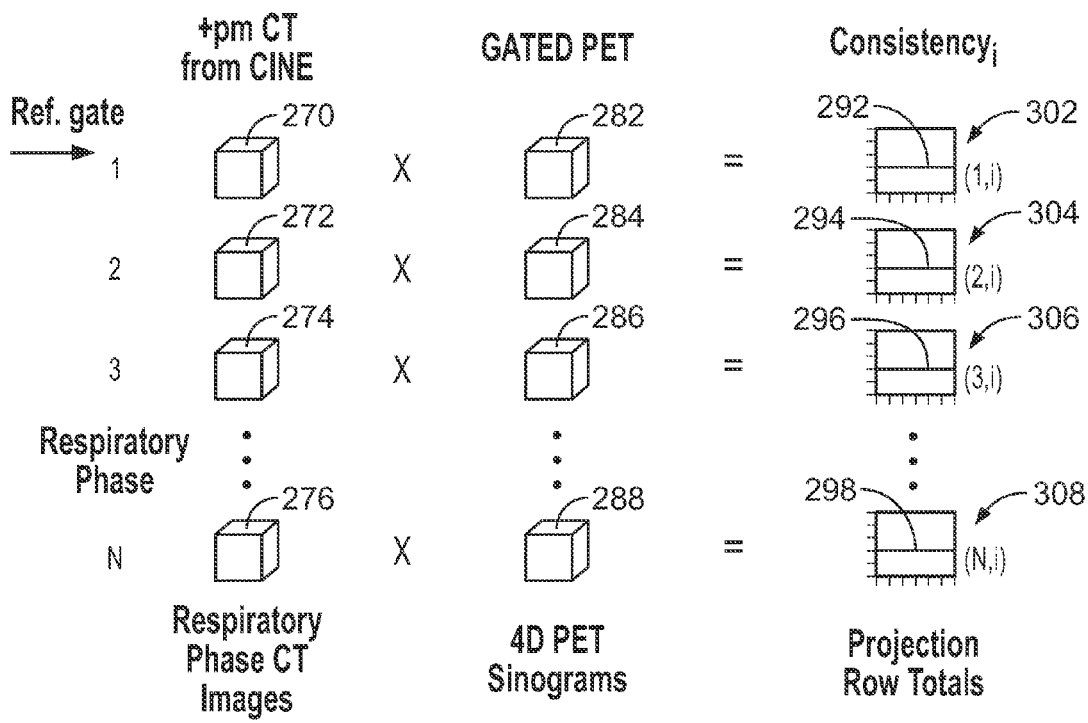
FIG. 6 is a simplified block diagram illustrating another portion of the method shown in FIG. 2.

Referring again to FIG. 2, at 112, the transforms acquired at 110, from the PET-PET registration, are utilized to generate a plurality of phase-matched CT images. These newly-derived CT images are used to update the per-bin consistency measurements. For example, as shown in FIG. 6, the phase-matched CT image 276 is used to update the consistency criterion for bin N. Accordingly, a phase-matched CT image 272 may be formed using the vectors $T_{31}$, a phase-matched CT image 274 may be formed using the vectors $T_{32}$, and a phase-matched CT image 276 may be formed using the vectors $T_3N$. Accordingly, at 112, the plurality of vectors are acquired and utilized to form the phase-matched CT images which are then used to update the consistency criterion for each bin.

Referring again to FIG. 2, at 114, the initial consistency conditions acquired at 104 are revised. For example, FIG. 6 illustrates an exemplary method of revising the consistency conditions. In various embodiments, the CT images 272-276 are again used in conjunction with gated PET bins 282-288 to generate an updated set of consistency measurements per bin. Moreover, a consistency condition 292-298 is calculated for each respective bin of updated ("+pm CT") attenuation and emission data. The consistency conditions may be calculated using, for example, a Helgason-Ludwig consistency condition (HLCC) algorithm (Eq. 1). As shown in FIG. 6, a graph 302 illustrates the consistency conditions for the bin 282, a graph 304 illustrates the consistency conditions for the bin 284, a graph 306 illustrates the consistency conditions for the bin 286, and a graph 308 illustrates the consistency conditions for the bin 288.

Figure 7:
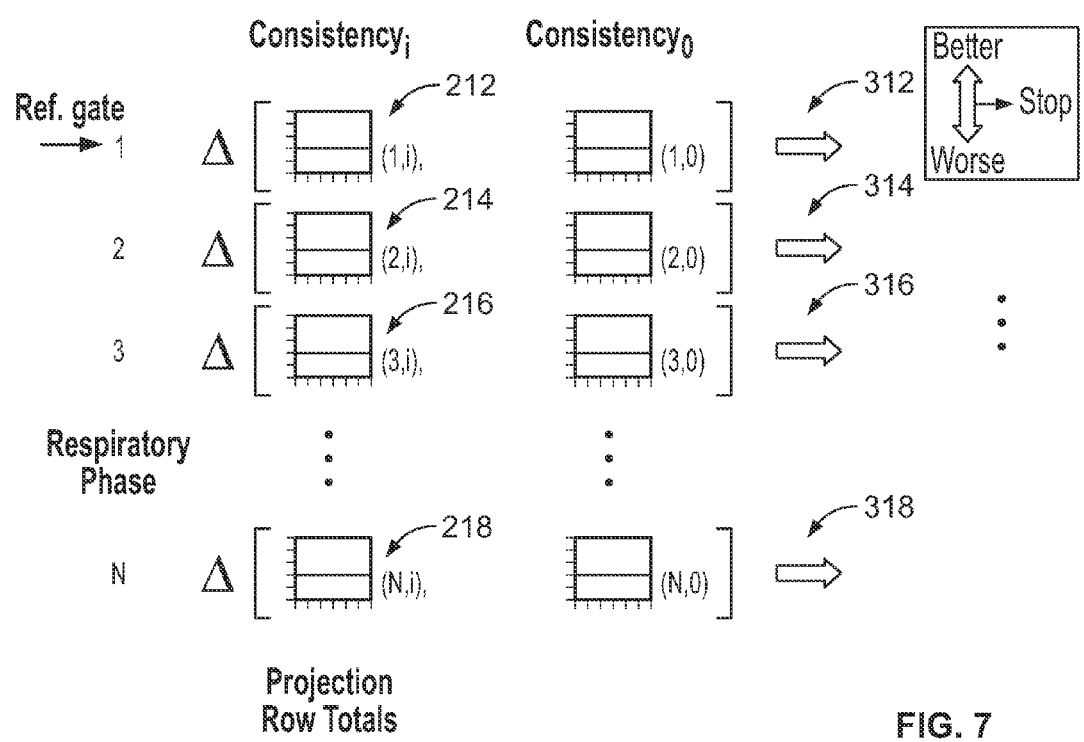
FIG. 7 is a simplified block diagram illustrating another portion of the method shown in FIG. 2.

At 116, an objective function is updated or revised. More specifically, as described above, the consistency conditions are initially calculated in 104. More specifically, and as shown in FIG. 3, the PET image having the most consistency with the CT image 60, determined using the consistency conditions, is identified and thus the consistency map is the flattest as a function of angle (for instance) indicating the that the one set of PET projection data is substantially most consistent with the CT image 60. Accordingly, at 116, the attenuation map from the CT may be revised or re-calculated to generate a second set of consistency maps which may be better or worse than the original consistency maps shown in FIG. 3. For example, FIG. 7 illustrates an exemplary initial consistency map 312 that may be generated and compared to the current consistency map 212 to determine whether the consistency between the PET image 282 and the CT images 270-276 has either increased, decreased, or remained the same as compared to the consistency generated using the initial hCT image 60. Additionally, a consistency map 314 may be generated and compared to the consistency map 214, a consistency map 316 may be generated and compared to the consistency map 216, and a consistency map 318 may be generated and compared to the consistency map 218.

Figure 8:
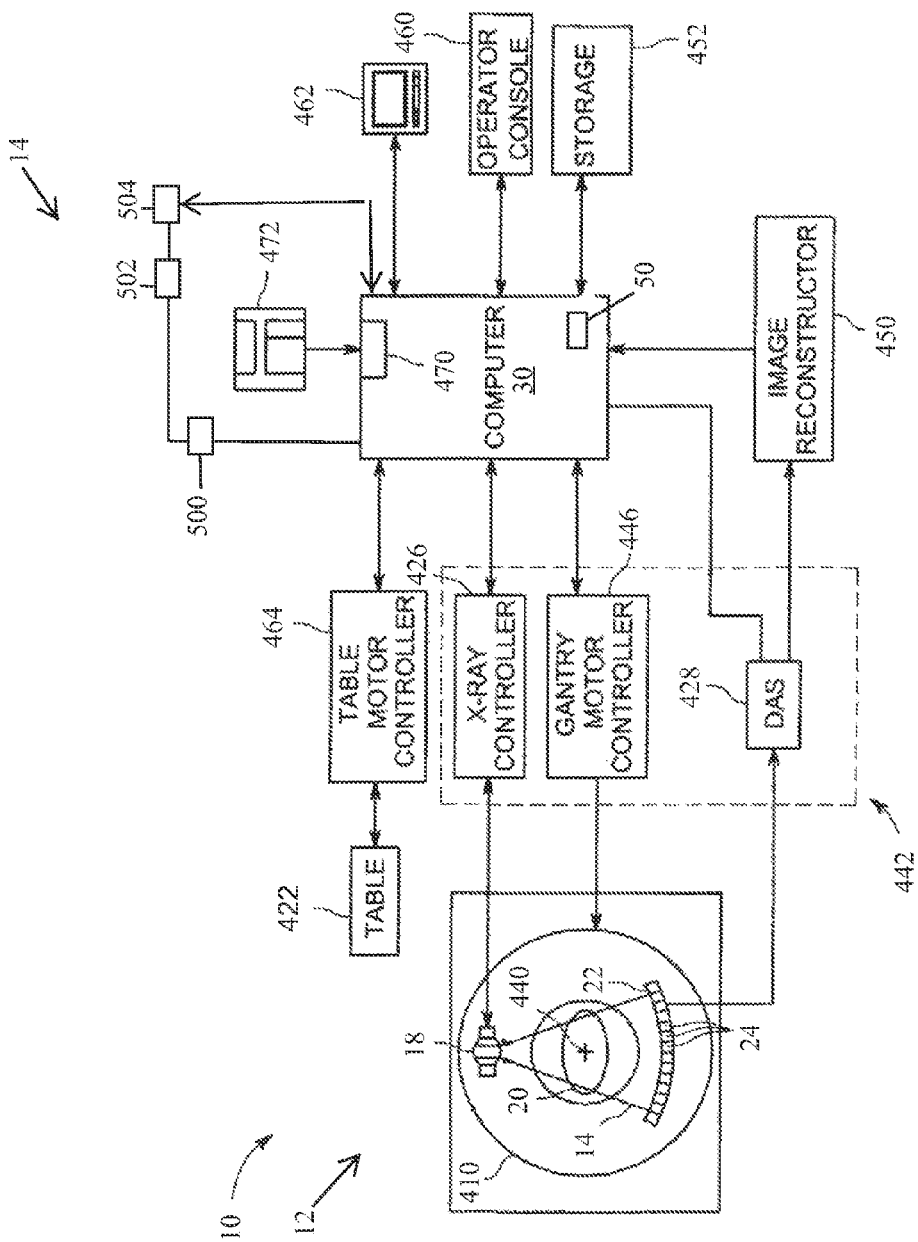
FIG. 8 is a block schematic diagram of a portion of the imaging system illustrated in FIG. 1.

Referring again to FIG. 2, at 118, steps 108-116 are iteratively repeated until the change in the consistency conditions are within a predetermined threshold. In various embodiments, if the consistency conditions are not within a predetermined threshold, then at 120, the emission dataset is again compared to the updated CT images acquired at 114 and the method proceeds to step 108. In various other embodiments, if the consistency conditions are within a predetermined threshold, then at 122, a final global non-rigid registration is performed on the PET images. In operation, the non-rigid registration is utilized to perform the motion correction on the information within the bins 282-288. In operation, the non-rigid registration or elastic registration includes non-rigid transformations. These non-rigid transformations allow local warping of image features and provide registrations that account for local deformations. At 124, the transformed PET images acquired at 122 are averaged together or the median result per voxel from the set of transformed PET images is used to generate a three-dimensional (3D) rigid-registration (RRA) volume. At 126, the 3D RRA volume is utilized FIG. 8 is a schematic block diagram of the imaging system 10 (shown in FIG. 1). As described above, the imaging system 10 includes the CT imaging system 12 and the PET imaging system 14. The imaging system 10 allows for multiple scans in different modalities to facilitate an increased diagnostic capability over single modality systems. The CT imaging system 12 includes the gantry 16 that has the x-ray source 18 that projects the beam of x-rays 14 toward the imaging detector 22 on the opposite side of the gantry 16. The imaging detector 22 includes the plurality of detector elements 24 that are arranged in rows and channels that together sense the projected x-rays that pass through an object, such as the subject 20. The imaging system 10 also includes the computer 30 that receives the projection data from the imaging detector 22 and processes the projection data to reconstruct an image of the subject 20.

In operation, operator supplied commands and parameters are used by the computer 30 to provide control signals and information to reposition a motorized table 422. More specifically, the motorized table 422 is utilized to move the subject 20 into and out of the gantry 16. Particularly, the table 422 moves at least a portion of the subject 20 through a gantry opening 424 that extends through the gantry 16.

The imaging system 10 also includes the image reconstruction module 50 that is configured to implement various methods described herein. As discussed above, the detector 22 includes the plurality of detector elements 24. Each detector element 24 produces an electrical signal, or output, that represents the intensity of an impinging x-ray beam and hence allows estimation of the attenuation of the beam as it passes through the subject 20. During a scan to acquire the x-ray projection data, the gantry 16 and the components mounted thereon rotate about a center of rotation 440. FIG. 8 shows only a single row of detector elements 24 (i.e., a detector row). However, the multislice detector array 22 includes a plurality of parallel detector rows of detector elements 24 such that projection data corresponding to a plurality of slices can be acquired simultaneously during a scan.

Rotation of the gantry 16 and the operation of the x-ray source 18 are governed by a control mechanism 442. The control mechanism 442 includes an x-ray controller 426 that provides power and timing signals to the x-ray source 18 and a gantry motor controller 446 that controls the rotational speed and position of the gantry 16. A data acquisition system (DAS) 428 in the control mechanism 442 samples analog data from detector elements 24 and converts the data to digital signals for subsequent processing. For example, the subsequent processing may include utilizing the module 50 to implement the various methods described herein. An image reconstructor 450 receives the sampled and digitized x-ray data from the DAS 428 and performs high-speed image reconstruction. The reconstructed images are input to the computer 30 that stores the image in a storage device 452. Optionally, the computer 30 may receive the sampled and digitized x-ray data from the DAS 428 and perform various methods described herein using the module 50. The computer 30 also receives commands and scanning parameters from an operator via a console 460 that has a keyboard. An associated visual display unit 462 allows the operator to observe the reconstructed image and other data from computer.

The operator supplied commands and parameters are used by the computer 30 to provide control signals and information to the DAS 428, the x-ray controller 426 and the gantry motor controller 446. In addition, the computer 30 operates a table motor controller 464 that controls the motorized table 422 to position the subject 20 in the gantry 16. Particularly, the table 422 moves at least a portion of the subject 20 through the gantry opening 424 as shown in FIG. 1.

Referring again to FIG. 8, in one embodiment, the computer 30 includes a device 470, for example, a floppy disk drive, CD-ROM drive, DVD drive, magnetic optical disk (MOD) device, or any other digital device including a network connecting device such as an Ethernet device for reading instructions and/or data from a non-transitory computer-readable medium 472, such as a floppy disk, a CD-ROM, a DVD or an other digital source such as a network or the Internet, as well as yet to be developed digital means. In another embodiment, the computer 30 executes instructions stored in firmware (not shown). The computer 30 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 18 and the imaging detector 22 are rotated with the gantry 16 within the imaging plane and around the subject 20 to be imaged such that the angle at which an x-ray beam 474 intersects the subject 16 constantly changes. A group of x-ray attenuation measurements, i.e., projection data, from the imaging detector 22 at one gantry angle is referred to as a "view". A "scan" of the subject 20 comprises a set of views made at different gantry angles, or view angles, during one revolution of the x-ray source 18 and the imaging detector 20. In a CT scan, the projection data is processed to reconstruct an image that corresponds to a two dimensional slice taken through the subject 20.

The imaging system 10 also controls the operation of the PET imaging system 14. Accordingly, in various embodiments, the imaging system 10 may also include a coincidence processor 502 that is coupled between a PET detector 500 and a PET scanner controller 504. The PET scanner controller 504 is utilized to control the operation of the PET system 14. In various embodiments, the PET scanner controller 504 may be coupled to the computer 30. In operation, the signals output from the detector 500 are input to the coincidence processor 502. In various embodiments, the coincidence processor 502 assembles information regarding each valid coincidence event into an event data packet that indicates when the event took place and the position of a detector that detected the event. The valid events may then be conveyed to the controller 504 and/or the computer 30 to reconstruct an image.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for reducing, in an image, motion related imaging artifacts, said method comprising:
   obtaining a single image volume of a subject using a computed tomography (CT) imaging system;
   obtaining a plurality of projection data of the subject using a positron emission tomography (PET) imaging system;
   calculating a plurality of initial consistency values using the CT image and the plurality of PET projection data, wherein each consistency value represents at least one of a sum or row-sum of all emission data acquired in a view and is view angle independent;
   generating a plurality of attenuation-corrected PET images;
   generating a PET motion correction including a series of transformation matrices;
   utilizing the combination of transformation matrices and initial consistency values to generate transformed CT image volumes to match the plurality of PET projection data;
   calculating updated consistency values using the transformed CT image volumes;
   using objective functions to iteratively determine changes in the updated and initial consistency values; and
   generating a final attenuation-matched PET reconstruction and motion correction if the determined change is less than a predetermined threshold, and if the determined change is not less than the predetermined threshold, generating a revised set of attenuation corrected PET images using the transformed CT image volumes, and using objective functions to iteratively determine changes in the updated and initial consistency values.

2. The method of claim 1, wherein generating a plurality of consistency values comprises:
   sorting the PET images into separate field-of-view bins using a gating system; and
   generating a plurality of consistency values for each bin of PET images.

3. The method of claim 2, further comprising:
   sorting the PET images into separate field-of-view bins;
   identifying a PET bin having a maximum consistency with the single CT image, wherein the PET bin having a most linear consistency condition with the single CT image among the separate field-of-view bins is identified; and
   reconstructing a plurality of PET images using the identified bin.

4. The method of claim 1, further comprising:
   sorting the PET images into separate field-of-view bins;
   generating a first plurality of transformation vectors for each of PET bins;
   selecting at least one of the PET bins as a reference bin; and
   performing a non-rigid registration of the PET bins using the transformation vectors.

5. The method of claim 4, further comprising:
   generating a second set of transformation vectors using the consistency values and the first plurality of transformation vectors; and
   transforming the single CT image based on the second set of transformation vectors and the first plurality of transformation vectors.

6. The method of claim 1, further comprising:
   sorting the PET images into separate field-of-view bins;
   generating a first plurality of transformation vectors for each of PET bins; and
   applying the first plurality of transformation vectors to the single CT image to generate CT attenuation information.

7. The method of claim 1, further comprising iteratively revising the consistency values until a predetermined threshold is met.

8. A dual-modality imaging system comprising:
a computed tomography (CT) imaging system;
a positron emission tomography (PET) imaging system; and
a processor coupled to the CT and PET imaging systems, the processor configured to obtain a single image of a subject using the CT imaging system;
obtain a plurality of images of the subject using the PET imaging system;
generate a plurality of consistency values, wherein each consistency value represents at least one of a sum or row-sum of all emission data acquired in a view and is view angle independent; and
utilize the plurality of consistency values to register the CT image and the plurality of PET images.

9. The multi-modality imaging system of claim 8, wherein the processor is further configured to:
sort the PET images into separate field-of-view bins; and
generate a plurality of consistency values for each bin of PET images.

10. The multi-modality imaging system of claim 8, wherein the processor is further configured to:
sort the PET images into separate field-of-view bins;
identify a PET bin having a maximum consistency with the single CT image, wherein the PET bin having a most linear consistency condition with the single CT image among the separate field-of-view bins is identified; and
reconstruct a plurality of PET images using the identified bin.

11. The multi-modality imaging system of claim 8, wherein the processor is further configured to:
sort the PET images into separate field-of-view bins;
generate a first plurality of transformation vectors for each of PET bins;
select at least one of the PET bins as a reference bin; and
perform a non-rigid registration of the PET bins using the transformation vectors.

12. The multi-modality imaging system of claim 8, wherein the processor is further configured to:
generate a second set of transformation vectors using the consistency values and the first plurality of transformation vectors; and
transform the single CT image based on the second set of transformation vectors and the first plurality of transformation vectors.

13. The multi-modality imaging system of claim 8, wherein the processor is further configured to:
sort the PET images into separate field-of-view bins;
generate a first plurality of transformation vectors for each of PET bins; and
apply the first plurality of transformation vectors to the single CT image to generate CT attenuation information.

14. The multi-modality imaging system of claim 8, wherein the processor is further configured to iteratively revise the consistency values until a predetermined threshold is met.

15. A non-transitory computer readable medium encoded with a program programmed to instruct a computer to:
obtain a single image of a subject using a computed tomography (CT) imaging system;
obtain a plurality of images of the subject using a positron emission tomography (PET) imaging system;
generate a plurality of consistency values, wherein each consistency value represents at least one of a sum or row-sum of all emission data acquired in a view and is view angle independent; and
utilize the plurality of consistency values to register the CT image and the plurality of PET images.

16. The non-transitory computer readable medium of claim 15, further programmed to instruct a computer to:
sort the PET images into separate field-of-view bins; and
generate a plurality of consistency values for each bin of PET images.

17. The non-transitory computer readable medium of claim 15, further programmed to instruct a computer to:
sort the PET images into separate field-of-view bins;
identify a PET bin having a maximum consistency with the single CT image, wherein the PET bin having a most linear consistency condition with the single CT image among the separate field-of-view bins is identified; and
reconstruct a plurality of PET images using the identified bin.

18. The non-transitory computer readable medium of claim 15, further programmed to instruct a computer to:
sort the PET images into separate field-of-view bins;
generate a first plurality of transformation vectors for each of PET bins;
select at least one of the PET bins as a reference bin; and
perform a non-rigid registration of the PET bins using the transformation vectors.

19. The non-transitory computer readable medium of claim 15, further programmed to instruct a computer to:
generate a second set of transformation vectors using the consistency values and the first plurality of transformation vectors; and
transform the single CT image based on the second set of transformation vectors and the first plurality of transformation vectors.

20. The non-transitory computer readable medium of claim 15, further programmed to instruct a computer to:
sort the PET images into separate field-of-view bins;
generate a first plurality of transformation vectors for each of PET bins; and
apply the first plurality of transformation vectors to the single CT image to generate CT attenuation information.

* * * * *